(12) United States Patent
Yamada et al.

(10) Patent No.: US 10,527,581 B2
(45) Date of Patent: Jan. 7, 2020

(54) MOLECULAR DETECTION APPARATUS, MOLECULAR DETECTION METHOD, AND ORGANIC PROBE

(71) Applicant: KABUSHIKI KAISHA TOSHIBA, Minato-ku (JP)

(72) Inventors: Ko Yamada, Yokohama (JP); Reiko Yoshimura, Kawasaki (JP); Hirohisa Miyamoto, Kamakura (JP); Norikazu Osada, Meguro (JP); Mitsuhiro Oki, Kawasaki (JP); Hiroko Nakamura, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 112 days.

(21) Appl. No.: 15/699,161

(22) Filed: Sep. 8, 2017

(65) Prior Publication Data

US 2018/0059053 A1 Mar. 1, 2018

Related U.S. Application Data

(63) Continuation of application No. PCT/JP2015/004619, filed on Sep. 10, 2015.

(51) Int. Cl.
*G01N 27/27* (2006.01)
*G01N 27/414* (2006.01)

(52) U.S. Cl.
CPC ..... *G01N 27/4148* (2013.01); *G01N 27/4141* (2013.01)

(58) Field of Classification Search
CPC ............. G01N 27/4148; G01N 27/414; G01N 27/403; G01N 27/27; G01N 27/00

USPC ......................................................... 436/104
See application file for complete search history.

(56) References Cited

U.S. PATENT DOCUMENTS

| 2003/0165873 | A1 | 9/2003 | Come et al. |
| 2008/0283875 | A1 | 11/2008 | Mukasa et al. |
| 2009/0032701 | A1 | 2/2009 | Rodier |
| 2009/0078862 | A1 | 3/2009 | Rodier et al. |
| 2013/0273665 | A1 | 10/2013 | Swager et al. |

FOREIGN PATENT DOCUMENTS

| CN | 102318035 | 1/2012 |
| EP | 1 364 212 | 11/2003 |
| EP | 2 828 647 | 1/2015 |
| EP | 2 848 929 A1 | 3/2015 |

(Continued)

OTHER PUBLICATIONS

Kawada et al, JP 2010-038840 A, English Machine Translation, Feb. 2010, obtained on May 2, 2019, pp. 1-51. (Year: 2019).*

(Continued)

*Primary Examiner* — Christine T Mui
(74) *Attorney, Agent, or Firm* — Oblon, McClelland, Maier & Neustadt, L.L.P.

(57) ABSTRACT

A molecular detection apparatus according to an embodiment includes a detector and a discriminator. The detector includes a plurality of detection cells, where the plurality of detection cells include at least an organic probe containing a cyano group or a nitro group as a neighboring group of a reactive group. The discriminator discriminates a substance to be detected by signal patterns of the plurality of detection cells.

13 Claims, 7 Drawing Sheets

(56) References Cited

FOREIGN PATENT DOCUMENTS

| JP | 2005-516580 | 6/2005 | | |
|----|----|----|----|----|
| JP | 3963474 | 6/2007 | | |
| JP | 2008-216083 | 9/2008 | | |
| JP | 2010-019688 | 1/2010 | | |
| JP | 2010-025719 | 2/2010 | | |
| JP | 2010-038569 | 2/2010 | | |
| JP | 2010-038840 | 2/2010 | | |
| JP | 2010-038840 A | * 2/2010 | ............ | G01N 27/04 |
| JP | 2010-139269 | 6/2010 | | |
| JP | 2010-535345 | 11/2010 | | |
| JP | 2011-080798 | 4/2011 | | |
| JP | 4827144 | 9/2011 | | |
| JP | 2012-247189 | 12/2012 | | |
| JP | 2013-253825 | 12/2013 | | |
| JP | 2015-515622 | 5/2015 | | |
| WO | 1996/030750 | 10/1996 | | |
| WO | 2002/070662 | 9/2002 | | |
| WO | 2009/018305 | 2/2009 | | |
| WO | 2013/184222 | 12/2013 | | |

OTHER PUBLICATIONS

"Novel pyrenehexafluoroisopropanol derivative-decorated single-walled carbon nanotubes for detection of nerve agents by strong hydrogen-bonding interaction" by Lingtao Kong et al.: Analyst: 2010. 135; pp. 368-374.

"Monolayer-Dimensional 5,5'-Bis(4-hexylphenyl)-2,2'-bithiophene Transistors and Chemically Responsive Heterostructures" by Jia Huang et al.: Advanced Materials 2008; 20, pp. 2567-2572.

"Sub-ppt gas detection with pristine graphene" by Gugang Chen et al.; Applied Physics Letters; 101, 053119 (2012).

\* cited by examiner

[ORGANIC COMPOUND 1]          [ORGANIC COMPOUND 2]

[ORGANIC COMPOUND 3]   [ORGANIC COMPOUND 4]   [ORGANIC COMPOUND 5]

MOLECULAR DETECTION APPARATUS, MOLECULAR DETECTION METHOD, AND ORGANIC PROBE

CROSS-REFERENCE TO RELATED APPLICATIONS

This application is based upon and claims the benefit of priority from International Patent Application No. PCT/JP2015/004619, filed on Sep. 10, 2015; the entire contents of which are incorporated herein by reference.

FIELD

Embodiments described herein generally relate to a molecular detection apparatus, a molecular detection method, and an organic probe.

BACKGROUND

A water heater or the like for household use is provided with an apparatus that detects carbon monoxide generated when incomplete combustion occurs and notifies the risk thereof at an early stage. Such a gas component considerably affects a human body. According to the guidelines from LP gas safety committee, it is set that a carbon monoxide concentration of approximately 200 ppm (parts per million) causes headaches. Although various methods have been known as a method of detecting a gas component having a relatively higher concentration, the detection methods have been limited for detecting the gas component having a concentration in the order of ppb (parts per billion) to ppt (parts per trillion), which corresponds to an extremely low concentration.

At a disaster site or a site at which an act of terrorism occurs or the like, it has been desired to sense the risk in advance by detecting an extremely small amount of the gas component. The gas component having an extremely low concentration is often detected by use of large equipment in research facilities. In this case, a large sized installation type apparatus, which is expensive and has large weight and volume, such as a gas chromatography or a mass spectrometer is required. Under such circumstances, it has been required to provide an apparatus that is capable of detecting the gas component having the extremely low concentration in real time, in other words, an apparatus that has a smaller weight and volume and a better portability and enables selective and higher sensitive detection of the gas component having the extremely low concentration in the order of ppt to ppb.

As a detection element for the gas component having a low concentration, for example, an element has been known that has a conductive layer in which a surface of a carbon nanostructure is surface modified with a substance that selectively reacts with or adsorbs a specific substance and measures a potential difference or the like that changes depending on the gas component that has adhered to the surface of the carbon nanostructure. In such a detection element, there is a possibility that it is impossible to accurately detect a detection target gas component when a component or the like similar to the detection target gas component is mixed in the gas obtained from, for example, the air as impurities. Besides, the detection substances are limited to alcohol, nitrogen oxide, and so on whose molecular structure is simple.

DETAILED DESCRIPTION

A molecular detection apparatus according to an embodiment includes: a detector which includes a plurality of detection cells having at least an organic probe containing a cyano group or a nitro group as a neighboring group of a reactive group; and a discriminator which discriminates a substance to be detected by signal patterns of the plurality of detection cells.

Hereinafter, there will be explained a molecular detection apparatus and a molecular detection method according to embodiments with reference to the drawings. In the embodiments, substantially the same constituent elements are denoted by the same reference signs and a description thereof will be omitted in some case. The drawings are schematic, and a relation of the thickness and the planar dimension of each part, a thickness ratio among parts, and so on may differ from actual ones.

Figure 1:
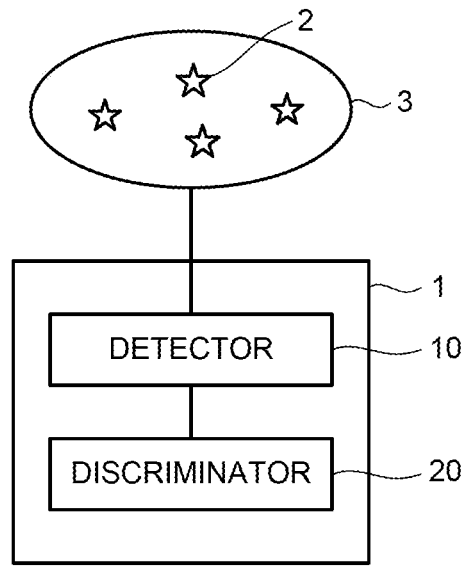
FIG. 1 is a block diagram illustrating a molecular detection apparatus according to an embodiment.
Figure 2:
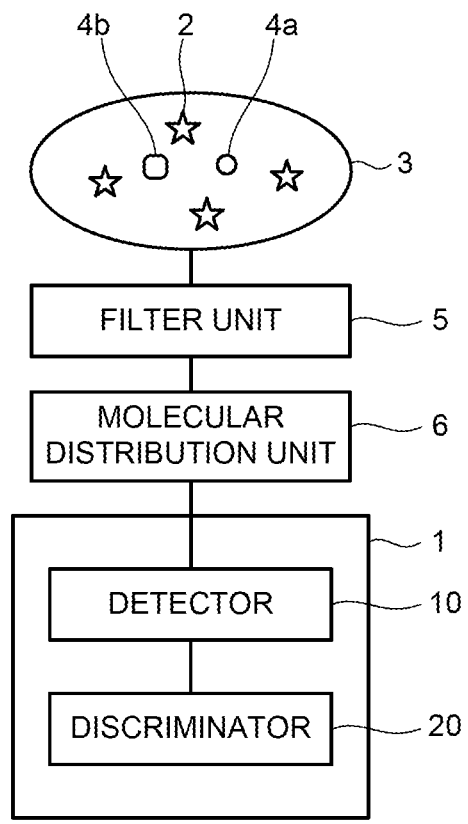
FIG. 2 is a block diagram illustrating a modified example of the molecular detection apparatus illustrated in FIG. 1.

FIG. 1 is a block diagram illustrating a molecular detection apparatus according to the embodiment. A molecular detection apparatus 1 illustrated in FIG. 1 is, for example, an apparatus that detects, from detection target gas 3 containing substances to be detected 2 generated from a gas generation source, the substance to be detected 2, and includes a detector 10 and a discriminator 20. The target gas 3 containing the substances to be detected 2 is, first sent to the detector 10 of the molecular detection apparatus 1. Here, the detection target gas 3 sometimes contains, as an impurity, substances having a molecular weight, a molecular structure or the like similar to those of the substance to be detected 2. Further, as illustrated in FIG. 2, the substances to be detected 2 drifting in the air often exist in a state where the substances to be detected 2 are mixed with various foreign substances 4 (4a and 4b) such as odor components and fine particles. From those perspectives, as illustrated in FIG. 2, the detection target gas 3 may be sent to the detector 10 of the molecular detection apparatus 1 after being preprocessed by a filter unit 5, a molecular distribution unit 6, and the like beforehand.

For the filter unit 5 out of the devices of preprocess, a generally-used moderate-to-high performance filter or the like is used. The filter unit 5 removes particulate substances such as fine particles contained in the detection target gas 3. The detection target gas 3, from which the particulate substances are removed in the filter unit 5, is then sent to the molecular distribution unit 6. As the molecular distribution unit 6, there can be exemplified an apparatus that ionizes the detection target gas 3 to form an ionized substance group, applies voltage to the ionized substance group to allow the ionized substance group to fly at a speed proportional to the mass thereof, and separates an ionized substance of the substance to be detected 2 from the ionized substance group using a flight speed based on the difference in mass among ionized substances and a time of flight based on the flight speed. As the molecular distribution unit 6 as above, a device including an ionization unit, a voltage application unit, and a time-of-flight separation unit is used.

Figure 3:
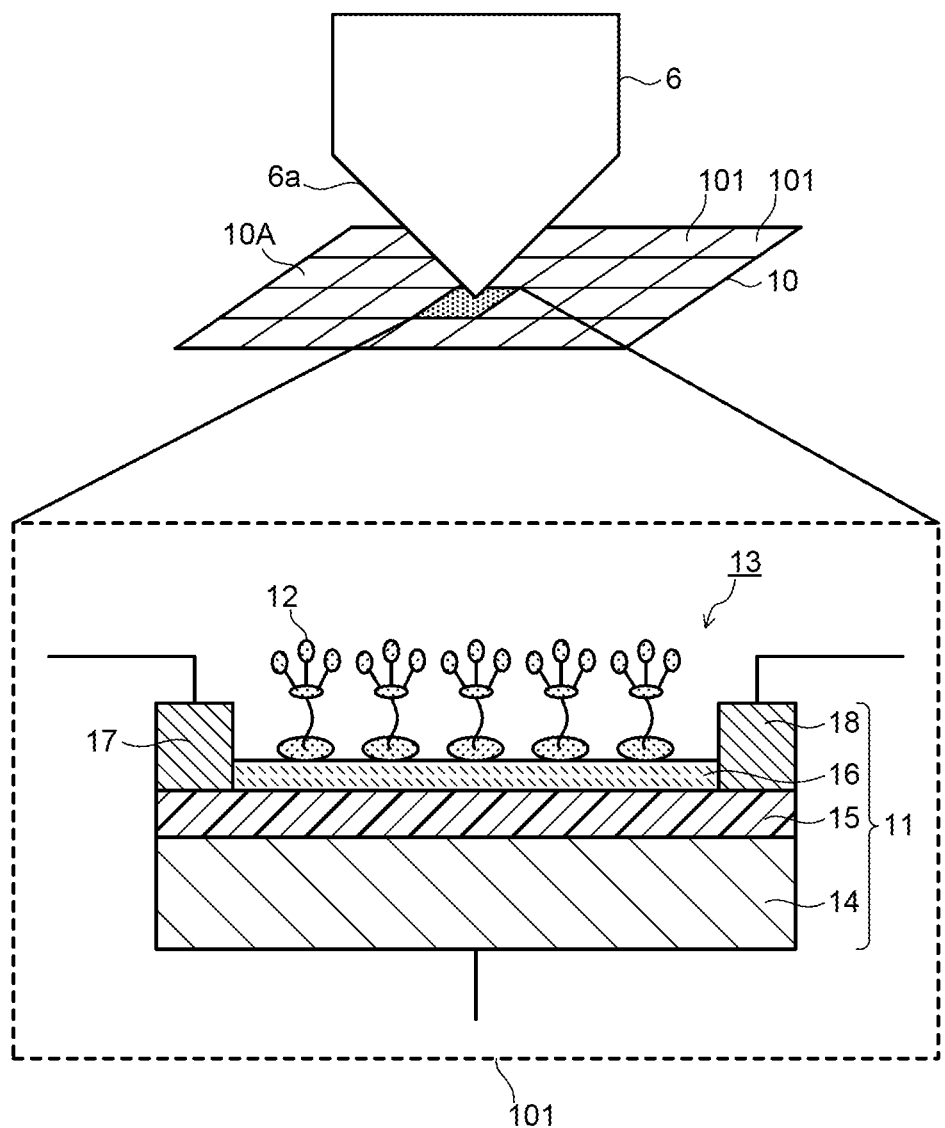
FIG. 3 is a view illustrating a configuration of a detector in the molecular detection apparatus according to the embodiment.

The target gas 3 containing the substances to be detected 2 is led to the detector 10 directly, or after being preprocessed by the devices such as the filter unit 5 and the molecular distribution unit 6. The detector 10, as illustrated in FIG. 3, includes a detection surface sectioned into a plurality of detection cells 101. Note that FIG. 3 illustrates a state where a detection surface 10A of the detector 10 is disposed to face an end part 6a of the molecular distribution unit 6, but the disposition of the detector 10 is not limited thereto. The plurality of detection cells 101 each include a sensor unit 11 and a detection element 13 having organic probes 12 provided at the sensor unit 11. FIG. 3 illustrates the detection element 13 using a graphene field effect transistor (GFET) for the sensor unit 11. The sensor unit 11 is not limited to the GFET, and may be a field effect transistor using carbon nanotube, a surface acoustic wave sensor, and so on.

The GFET serving as the sensor unit 11 includes a semiconductor substrate 14 that functions as a gate electrode, an insulating film 15 provided as a gate insulating layer on the semiconductor substrate 14, a graphene layer 16 provided as a channel on the insulating film 15, a source electrode 17 provided at one end of the graphene layer 16, and a drain electrode 18 provided at the other end of the graphene layer 16. The organic probes 12 are provided on the graphene layer 16 of the GFET 11. An organic compound selectively bonding to the substance to be detected 2 is used for the organic probe 12. The substances to be detected 2 that are led into the detector 10 are captured by the organic probes 12 on the graphene layer 16. Some impurities 4 cannot obtain an interaction with the organic probes 12, and are not captured by the detection element 13. Electrons transfer from the substance to be detected 2 captured by the organic probe 12 to the GFET 11, thereby electrical detection is performed. In this way, the target substance to be detected 2 is selectively detected.

An organic matter forming the organic probe 12 has a property of dissolving in a solvent. Thus, the organic probe 12 can be installed at the graphene layer 16 by applying a solution obtained by dissolving the organic matter in a solvent to the graphene layer 16. In order to easily obtain an interaction with graphene, the organic probe 12 preferably has a portion having such a structure as a pyrene ring. A molecule having such a structure as the pyrene ring interacts with a hexagonally shaped π electron system formed by carbon of the graphene, and forms an interaction state of what is called π-π stacking. Low-concentration probe molecules are dissolved in a solvent and the resultant is applied to the graphene, and thereby the π-π stacking is formed between the pyrene ring and the graphene and the probe molecules are aligned on the graphene to be fixed. By using such a self-alignment action, the organic probe 12 can be installed on the graphene layer 16. The organic compounds forming the organic probe 12 will be described in detail later.

When the substances to be detected 2 are captured by the organic probes 12 provided on the graphene layer 16, an output from the GFET 11 changes. The case of a single layer of graphene means that there is zero gap, and thus, the source electrode 17 and the drain electrode 18 are continuously electrified normally. When the number of graphene layers increases to two or three layers, a band gap is generated, but such a band gap in an actual system is relatively smaller than that considered from a strict theoretical value. When the gate insulating layer 15 has a dielectric constant approximately similar to that of a silicon oxide film, the source electrode 17 and the drain electrode 18 are often continuously electrified. Thus, the graphene layer 16 may be formed of a stack composed of about five graphene layers or less as well as the single layer structure of graphene.

The substance to be detected 2 flying in the vicinity of the organic probe 12 is attracted to the organic probe 12 by hydrogen bonding force, or comes into contact with the organic probe 12 in some cases. When the contact with the substance to be detected 2 occurs, an interchange of electrons occurs with the organic probe 12 and the organic probe 12 transmits an electrical change to the graphene layer 16 being in contact therewith. The electrical change transmitted from the organic probe 12 to the graphene layer 16 disturbs the flow of electricity between the source electrode 17 and the drain electrode 18, and thus the GFET 11 functions as a sensor. With the GFET 11 using the graphene layer 16 as a channel, even an extremely slight electrical change appears significantly as an output. As a result, it is possible to constitute the highly sensitive detection element 13. The sensor using the GFET 11 also has a tendency that electric current flows between the source electrode 17 and the drain electrode 18 without application of voltage to the gate electrode 14 because the graphene has a property as a zero-gap semiconductor. Thus, the GFET 11 functions as a sensor as it is. However, normally, the GFET 11 applies electric current between the source electrode 17 and the drain electrode 18 in a state of applying voltage to the gate electrode 14, and observes an electrical change of the gate electrode 14 when the organic probe 12 captures the substance to be detected 2.

In the detection of the substance to be detected 2 performed by the above-described detection element 13, as the transfer of electrons from the substance to be detected 2 that is captured by the organic probe 12 to the GFET 11 is higher, the function as the sensor is further increased. The sensor using the GFET 11 is regarded as the most sensitive FET sensor, and can improve sensitivity about three times as compared to a sensor using a carbon nanotube. Thus, using the detection element 13 in which the GFET 11 and the organic probes 12 are combined enables higher sensitive detection of the substance to be detected 2.

FIG. 3 illustrates the detection surface 10A on which the plurality of detection cells 101 are arranged in a grid pattern (an array pattern), but is not necessarily limited thereto. The plurality of detection cells 101 may be arranged linearly. At least some of the organic probes 12 provided at the graphene layers 16 of the plurality of detection cells 101 are different in bond strength with the substance to be detected 2. That is, the plurality of detection cells 101 include a plurality of the organic probes 12 different in the bond strength with the substance to be detected 2. All the organic probes 12 may be different in the bond strength with the substance to be detected 2, or some of the organic probes 12 may be different in the bond strength with the substance to be detected 2.

Figure 4A:
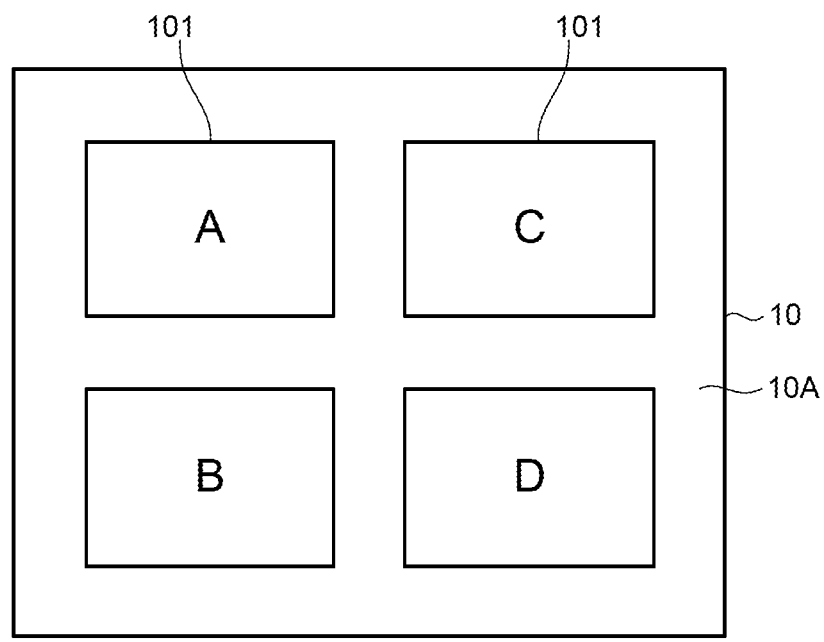
FIG. 4A is a view illustrating an example of a plurality of detection cells of the molecular detection apparatus according to the embodiment.
Figure 4B:
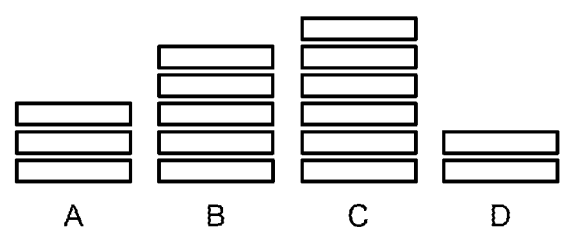
FIG. 4B is a view illustrating an example of a detection result of a substance to be detected by the plurality of detection cells illustrated in FIG. 4A.

FIG. 4A illustrates a grid-shaped sensor in which the detection surface 10A of the detector 10 is sectioned into four detection cells 101, that is a detection cell A, a detection cell B, a detection cell C, and a detection cell D. At least in some of the detection cells A to D, different types of the organic probes 12, that is the plurality of organic probes 12 different in the bond strength with the substance to be detected 2, are provided. The plurality of organic probes 12 each have an interaction with the substance to be detected 2, but are different in working strength (the bond strength) with the substance to be detected 2, and thus detection signals are different in intensity. FIG. 4B illustrates detection signals of the detection cells A to D. The detection signals from the detection cells A to D are different in signal intensity respectively due to the bond strength of the organic probe 12 with the substance to be detected 2.

The signals detected in the detection cells A to D are sent to the discriminator 20 to be signal-processed. The discriminator 20 converts each of the detection signals from the detection cells A to D into intensity and analyzes signal patterns based on intensity differences of these detection signals (for example, four detection signal patterns illustrated in FIG. 4B). The discriminator 20 stores therein signal patterns according to a substance to be detected and compares these signal patterns with the signal patterns detected in the detection cells A to D, to thereby discriminate the substance to be detected 2 detected in the detector 10. Such a signal process is called a pattern recognition method here. The pattern recognition method enables detection and discrimination of the substance to be detected 2 by signal patterns peculiar to the substance to be detected like a dactyloscopy, for example. Accordingly, selective and higher sensitive detection of a gas component (the substance to be detected 2) having an extremely low concentration in the order of ppt to ppb is enabled.

Application of the above-described pattern recognition method enables selective and higher sensitive detection and discrimination of the substance to be detected 2 even when impurities are mixed in the detection target gas 3 that is led to the detector 10. For example, in the case when the substance to be detected 2 is dimethyl methylphosphonate (DMMP, molecular weight: 124), which is a typical material for a toxic organophosphorus compound, there exist agricultural chemicals containing phosphoric acid such as dichlorvos having a similar chemical structure and organophosphorus pesticides, which are used often, such as malathion, chlorpyrifos, and diazinon. In order to prevent an erroneous detection of these substances, discrimination by such signal patterns as illustrated in FIG. 4B is effective. In other words, since the signal patterns detected in the detection cells A to D are different according to the above-described respective substances, application of the pattern recognition method enables selective and higher sensitive detection of the detection target substance even when an impurity that has a similar molecular weight and a similar constituent element is mixed.

Next, there is described in detail the organic probe 12 to be used for the plurality of detection cells A to D of the molecular detection apparatus 1 according to the embodiment. An organic compound forming the organic probe 12 has a hydroxy group (—OH) as a reactive group with respect to the substance to be detected 2. However, only the OH group hardly reacts with the gas component. Thus, for the purpose of enhancing a hydrogen bonding property, an organic compound where a functional group (a neighboring group) excellent in an inductive effect is introduced to a neighboring portion of the OH group is used. The plurality of organic probes 12 used for the plurality of detection cells A to D of the molecular detection apparatus 1 include an organic probe made of an organic compound having the OH group as the reactive group and at least one neighboring group which is disposed neighboring to the reactive group and is selected from the cyano group and the nitro group. Typical examples of such organic compounds forming the organic probe as stated above are illustrated in FIG. 5.

Figure 5:
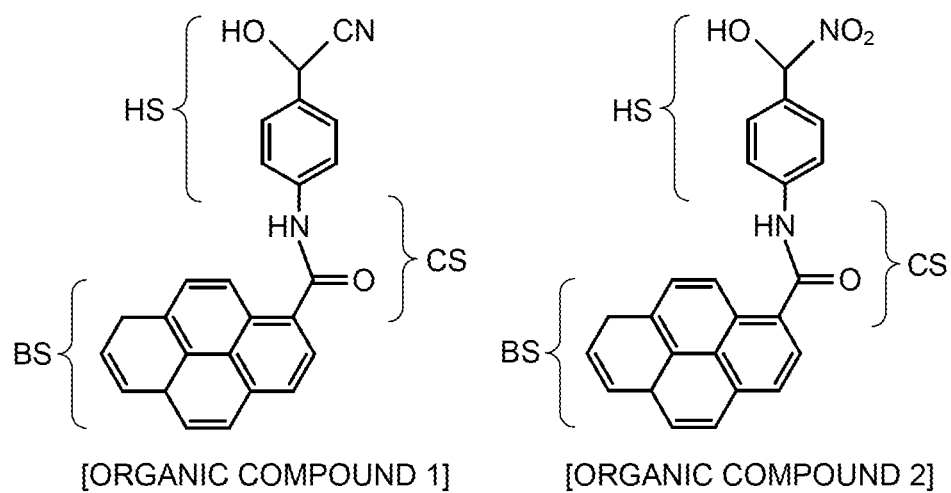
FIG. 5 is a view illustrating a first example of an organic compound used for an organic probe in the detector of the molecular detection apparatus according to the embodiment.

Between the organic compounds illustrated in FIG. 5, an organic compound 1 has the cyano group (—CN) as the neighboring group of the reactive group (OH group), and an organic compound 2 has the nitro group (—NO$_2$) as the neighboring group of the reactive group (OH group). As illustrated in FIG. 5, the organic compound forming the organic probe 12 includes a head portion HS having the reactive group and the neighboring group. The head portion HS is preferably a monovalent aromatic hydrocarbon group having the OH group and at least one neighboring group selected from the CN group and the NO$_2$ group, and more preferably a phenyl group having an alkyl group (carbon number: approximately 1 to 5) where the OH group and the CN group or the NO$_2$ group are bonded to the same carbon. It is not excluded that the aromatic hydrocarbon group (phenyl group) forming the head portion HS may have a substituent such as halogen and the alkyl group in addition to the reactive group and the neighboring group.

The organic compound forming the organic probe preferably has further a base portion BS serving as an installation portion for the graphene layer 16 or the like, and a connecting portion CS connecting the head portion HS and the base portion BS. The base portion BS is preferably a monovalent substituted or unsubstituted polycyclic aromatic hydrocarbon group having a polycyclic structure such as a pyrene ring, an anthracene ring, a naphthacene ring, or a phenanthrene ring, and more preferably the substituted or unsubstituted pyrene group. The connecting portion CS is a bivalent group, and it may be an alkylene group such as a methylene group or an ethylene group. The connecting portion CS is preferably an ether bond (—O—), an ester bond (—C(=O)O—), a carbonyl bond (—CO—), an amide bond (—NH—CO—), an imide bond (—CO—NH—CO—), and so on, and is more preferably the amide bond.

As concrete examples of the above-described organic compounds forming the organic probe, there can be cited cyanohydrin having the OH group and the CN group and derivatives thereof, and it is preferably the cyanohydrin derivative in consideration of the above-described head portion HS, connecting portion CS, and base portion BS. The cyanohydrin derivative can be obtained by, for example, reacting hydrogen cyanide (HCN), potassium cyanide (KCN), and so on with aromatic hydrocarbon having an aldehyde group (—CHO). Besides, the organic compound having the OH group and the $NO_2$ group can be obtained by, for example, a nitroaldol reaction. Note that a manufacturing method of the organic compound forming the organic probe 12 is not particularly limited, and it is possible to appropriately select a synthesis reaction in accordance with a target compound structure.

Figure 6:
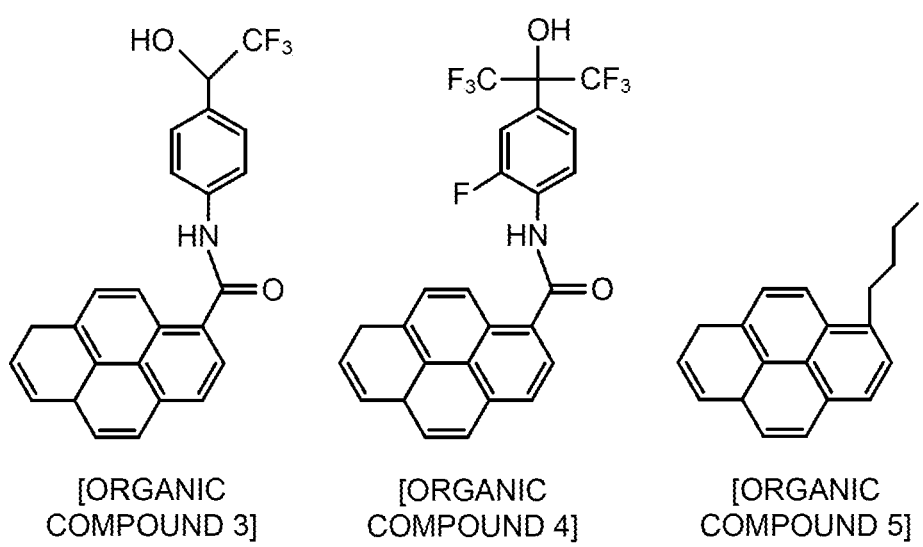
FIG. 6 is a view illustrating a second example of the organic compound used for the organic probe in the detector of the molecular detection apparatus according to the embodiment.

Incidentally, the organic compound forming the organic probe 12 is required to have the reactive group (OH group) and the neighboring group as described above. As the substituent (neighboring group) disposed neighboring to the reactive group (OH group), for example, there is known an alkyl group which is substituted by fluorine atoms such as a trifluoromethyl group (—$CF_3$) or a hexafluoroethyl group (—$C_2F_5$). As a structure having such a substituted alkyl group, there can be cited a 1,1,1,3,3,3-hexafluoro-2-phenyl-2-propanol structure (a structure A), an α-trifluoromethyl-benzyl alcohol structure (a structure B), and so on. These structures have an effect of enhancing activity of the reactive group (OH group) with fluorine having a high electronegativity. Concrete examples of an organic compound 3 where the structure A is applied and an organic compound 4 where the structure B is applied are illustrated in FIG. 6. The bond strength with the substance to be detected 2 of the organic compound 4 is different from that of the organic compound 3 because the numbers of neighboring groups ($CF_3$ groups) are different.

A degree of bonding with the substance to be detected 2 by the organic probe 12 can also be adjusted by the number of reactive groups (OH groups). In order to change the bonding degree with the substance to be detected 2 in the detection cell 101 where the organic compound 3 and the organic compound 4 are applied to the organic probes 12, a density of the organic probes 12 installed on the detection cell 101 may be adjusted. The organic probes 12 are installed on the graphene layer 16 under a state where, for example, an organic compound which does not have the reactive group (OH group) and have only the base portion BS such as the pyrene ring having the interaction with the graphene layer 16 such as an organic compound 5 illustrated in FIG. 6 is mixed with the organic compound 3 or the organic compound 4 so as to change the density of the organic probes 12. It is possible to change an electrical variation of the graphene layer 16 by a mixture ratio of the organic compound 5 with the organic compound 3 or the organic compound 4, that is, a ratio of the reactive group (OH group), to thereby change the intensity of the detection signal by the detection cell 101.

There is a limit in adjustment of the bond strength difference with the substance to be detected 2 by the organic probe 12 only by the above-described adjustment of the number of neighboring groups containing the fluorine atoms and adjustment of the density of the organic compounds having the reactive group (OH group). In the molecular detection apparatus 1 according to the embodiment, the organic probe 12 formed of the organic compound having the functional group containing nitrogen such as the cyano group (CN group) and the nitro group ($NO_2$ group) as the above-described neighboring group (the organic compound 1, the organic compound 2, and so on illustrated in FIG. 5) is used. It is possible to change the bond strength between the organic probe 12 and the substance to be detected 2 by substituting the neighboring group of the reactive group (OH group) into a substance other than fluorine. Since the cyano group (CN group) and the nitro group ($NO_2$ group) are also excellent in the inductive effect, the function of the reactive group (OH group) can be enhanced.

Figure 7:
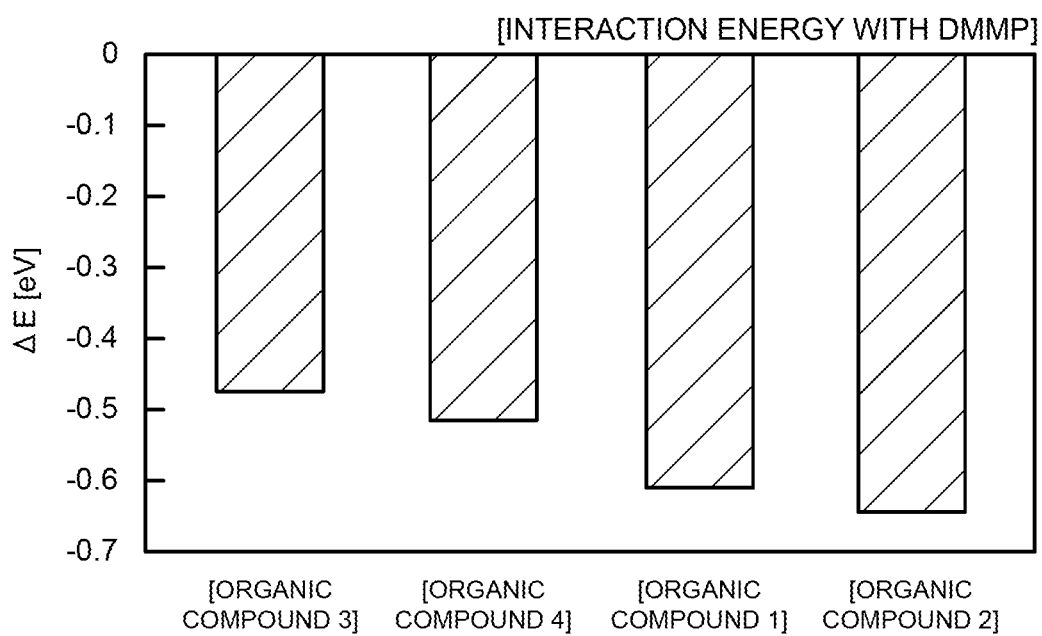
FIG. 7 is a view illustrating interaction energy between DMMP being the organic compound used for the organic probe in the detector of the molecular detection apparatus according to the embodiment.

Results where interaction energy between each of the organic compounds 1 to 4 and DMMP being a typical gas molecule is calculated by a density functional method (B3LYP/6–31+G(d, p)) are illustrated in FIG. 7. It can be seen that there are differences in the interaction energy between the organic compound and DMMP due to the difference in the induction effect of the neighboring group. The organic probe 12 formed of the organic compound having the cyano group (CN group) or the nitro group ($NO_2$ group) as the neighboring group can be used instead of the organic probe formed of the organic compound having a fluoroalkyl group as the neighboring group, or by being combined with such an organic probe. The organic probe formed of the organic compound having the cyano group or the nitro group as the neighboring group is used, and thereby, it is possible to diversify the bond strength difference between the organic probe 12 and the substance to be detected 2. Accordingly, it is possible to enable high-definition signal pattern based on the intensity difference of the detection signal of the substance to be detected 2 by the detection cell 101, and to enhance the detection accuracy of the substance to be detected 2. Further, it becomes possible to correspond to various kinds of substances to be detected 2.

Figure 8:
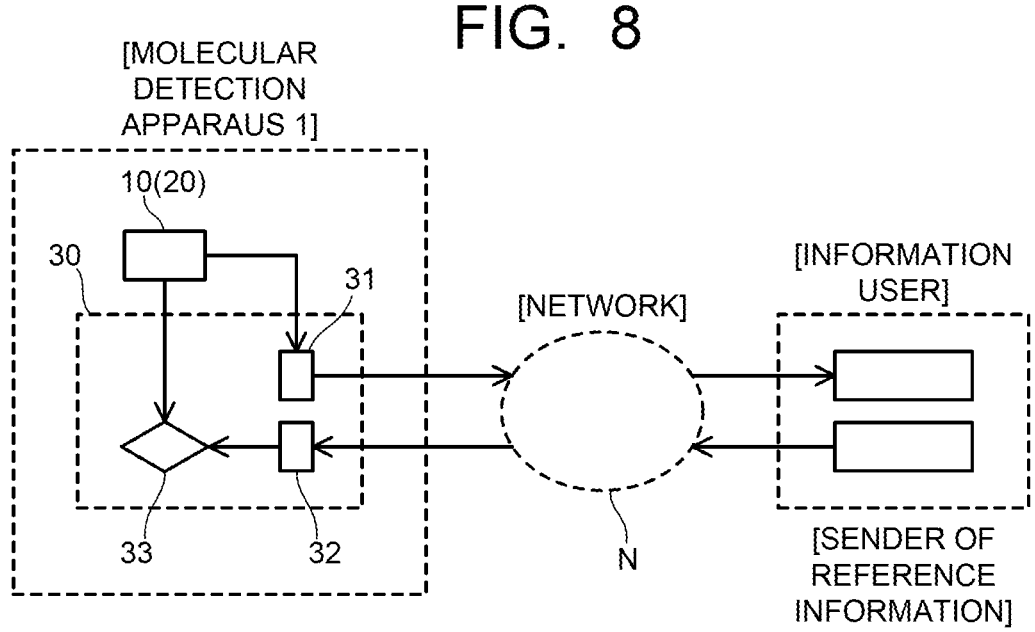
FIG. 8 is a view illustrating an information processing unit in the molecular detection apparatus according to the embodiment.

Detection and discrimination results of the substance to be detected 2 obtained by the molecular detection apparatus 1 may be transmitted over information network to be utilized. FIG. 8 illustrates the molecular detection apparatus 1 with an information processing unit 30 attached thereto or provided internally, the information processing unit 30 including at least one function selected from a function of transmitting detection information of the substance to be detected 2 over the information network and a function of checking between the detection information and reference information obtained from the information network. The information processing unit 30 includes an information transmitting unit 31 transmitting detection information of the substance to be detected 2, an information receiving unit 32 receiving reference information, and an information checking unit 33 checking between the detection information and the reference information. The information processing unit 30 may have only one of the information transmitting function, or the information receiving and information checking functions.

The information transmitting unit 31 transmits the detection information of the substance to be detected 2 to an information user over a network N. In order to check the detection information of the substance to be detected 2 with the existing reference information, the information receiving unit 32 obtains the reference information over the network N. The information checking unit 33 checks the obtained reference information with the detection information. Information is obtained from the external network N to be referred to, and thereby a function of carrying a lot of information and analyzing them can be replaced with an alternative externally. Consequently, further miniaturization of the molecular detection apparatus 1 is enabled to increase portability. Further, using the network N also makes it possible to obtain new signal patterns used by the pattern recognition method immediately. On the information receiving side, it is possible to take a next action based on this information. It is possible to use the molecular detection apparatus 1 in such a way that the portable molecular detection apparatus 1 is disposed at respective places and data to be obtained are collected from the respective places to be analyzed, and then the analyzed data are utilized for evacuation guidance under abnormal circumstances or the like. The network N and the molecular detection apparatus 1 are combined, and thereby a lot of use ways, which were not able to be achieved conventionally, are created and its industrial value improves.

According to the molecular detection apparatus 1 of the embodiment, the selective and higher sensitive detection of the gas component molecule having the extremely low concentration in the order of ppt to ppb is possible. Further, the detection sensitivity and the detection accuracy are enhanced by using the detector 10 and the discriminator 20, and thereby, it becomes possible to reduce the molecular detection apparatus 1 in size. Accordingly, it becomes possible to provide the molecular detection apparatus 1 where the portability and the detection accuracy are both enabled. It is possible for the molecular detection apparatus 1 according to the embodiment to effectively exert the functions at various sites such as at a disaster site or a site at which an act of terrorism occurs or the like.

EXAMPLE

In examples, dimethyl methylphosphonate (DMMP, molecular weight: 124) which is a toxic organophosphorus material, is used as a substance to be detected. DMMP being the substance to be detected is liquid at room temperature, has a flash point of 69° C., and a boiling point of 181° C. A vapor pressure is 79 Pa (at 20° C.). It has a property stable in liquid state at room temperature. In order to vaporize such liquid, it is general to increase a temperature to accelerate vaporization. Though, there are adopted a method aerating inert gas in the liquid to increase a surface area of the liquid, what is called bubbling, a method accelerating vaporization by spraying gas on a liquid surface, and so on as a more simple method.

A concentration of the gas obtained as stated above is approximately ppm (parts per million) to ppb (parts per billion), and the concentration is lowered by mixing the gas with the inert gas. The concentration of DMMP contained in the aerated nitrogen ($N_2$) gas by adopting the bubbling in the example is set to 10 ppm. The DMMP concentration is lowered by mixing second nitrogen gas with the gas. A gas concentration adjusting system is set such that the concentration can be arbitrary adjusted to be 100 ppt (parts per trillion) or more. It is difficult to check the concentration of gas of low density at several ppb or less with a mass spectrometer, and therefore, a collection tube is used. Since the collection tube adsorbs and condenses the gas component as time proceeds, it is possible to estimate the concentration of the original gas component by separating the gas component after the collection to be measured with the mass spectrometer.

A detection element in which a GFET and an organic probe are combined is prepared as follows. A graphene layer is formed by transferring graphite onto a substrate by an exfoliation method or by depositing graphene on a metal surface by means of a chemical vapor deposition method (CVD). A single layer or a plurality of layers of graphene deposited on the metal surface are transferred onto a polymer film, and the resultant polymer film is transferred again onto a desired semiconductor substrate for field effect transistor (FET) fabrication. For example, graphene is formed on a surface of a copper foil by CVD with flowing of a methane gas under a condition of approximately 1000° C. Next, a polymethyl methacrylate film is applied at 4000 rpm by a spin coating method, and the opposite surface of the copper foil film is etched with an ammonium persulfate 0.1 M solution, and thereby a graphene film floating in the solution is recovered. By doing this, the graphene film is transferred onto the polymethyl methacrylate film side. A surface of the graphene film is sufficiently cleaned, and then this is transferred onto a silicon substrate again. The redundant polymethyl methacrylate film is dissolved with acetone to be removed. A resist is applied onto the graphene transferred onto the silicon substrate to undergo patterning, and a pattern with a 10 μm electrode interval is formed by oxygen plasma. Electrodes are deposited to form an FET structure on which a source electrode and a drain electrode are provided. The graphene is disposed on an oxide film formed on the surface of the silicon substrate and an FET type sensor structure is formed in which the graphene is sandwiched between the source electrode and the drain electrode and the silicon substrate side is set as the gate electrode.

The graphene sensor has a tendency that electric current flows between the source and the drain without application of voltage to the gate electrode because the graphene has a property as a zero-gap semiconductor. Thus, it functions as a sensor as it is, and a detection signal can be obtained by collision of substances with the graphene. However, normally, electric current is applied between the source and the drain in a state of applying the gate voltage, and an electrical change of the gate electrode when the substances are in contact is observed.

Next, organic probes are provided on the surface of the graphene. The organic probe is installed in a manner that an organic compound is dissolved in a methanol solution at a concentration of 10 nM and a graphene sensor surface is immersed in the resultant solution for several minutes. For the organic probes, the organic compound 1, the organic compound 2, and the organic compound 3 described above are used. Working force of the organic probe with respect to the substance to be detected changes depending on an amount of the reactive group (OH group). Accordingly, an amount of the organic probe may be adjusted by mixing the organic compound forming the organic probe with the above-described organic compound 5 which does not have the reactive group (OH group). For example, when the solution of the organic compound 1 is used, it is possible to adjust a ratio between the organic compound 1 and the organic compound 5 into 1:1 by substituting 5 nM from among 10 nM of the solution with the organic compound 5.

Figure 9A:
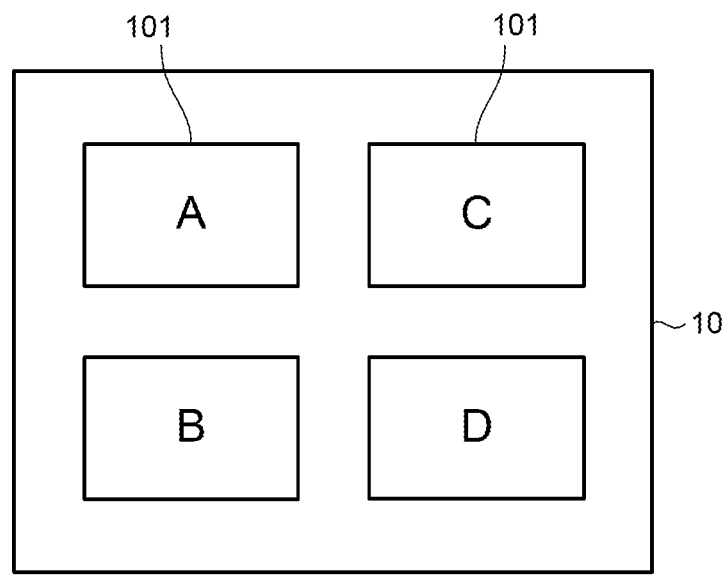
FIG. 9A is a view illustrating an example of a plurality of detection cells of the molecular detection apparatus of an example.

In the example, as illustrated in FIG. 9A, four detection cells A to D are provided on a detection surface of a detector, and the organic probes different from one another are respectively installed. The organic compound 3 is installed at the detection cell A as the organic probe. The organic compound 1 is installed at the detection cell B as the organic probe. The organic compound 2 is installed at the detection cell C as the organic probe. The organic compound 5 which does not have the reactive group is installed at the detection cell D to make it a standard cell indicating a reference. As described previously, the organic compound 1, the organic compound 2, and the organic compound 3 are respectively different in the bond strength with the substance to be detected (DMMP). Accordingly, it is possible to detect the substance to be detected (DMMP) by the detection cell according to the above-described pattern recognition method.

Figure 10:
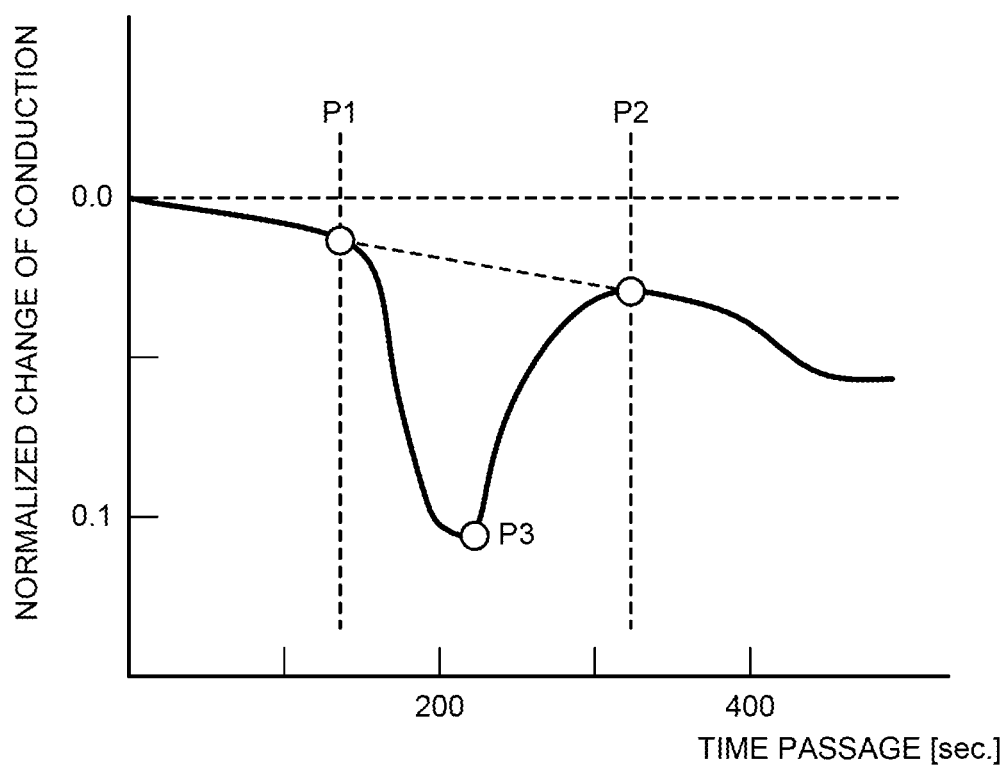
FIG. 10 is a view illustrating an example of a detected waveform of a substance to be detected by the molecular detection apparatus according to the example.

Gas containing DMMP as the substance to be detected is introduced into the detector including the above-described detection cells A to D to perform the detection of DMMP. The substances to be detected are respectively captured by the organic probes in the detection cells A to D. Since the organic probes in the detection cells A to D are respectively different in the bond strength with the substance to be detected, signals to be detected by the gate electrodes are also different respectively. Results of detection by the detection cells A to D are sent to a discriminator that processes signals, and are each converted into intensity. Although a method of converting into intensity can be variously considered, a value calculated from an area defined by P1, P2 and P3 being a tip of a peak in FIG. 10 is set as the intensity. However, the conversion method is not necessarily limited to this method.

Figure 9B:
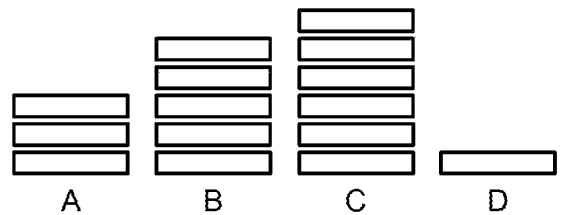
FIG. 9B is a view illustrating a first example of a detection result of a substance to be detected by the plurality of detection cells illustrated in FIG. 9A.
Figure 9C:
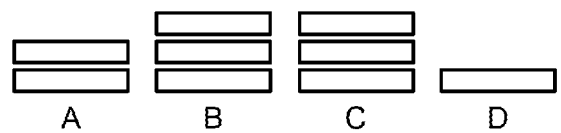
FIG. 9C is a view illustrating a second example of the detection result of the substance to be detected by the plurality of detection cells illustrated in FIG. 9A.
Figure 9D:
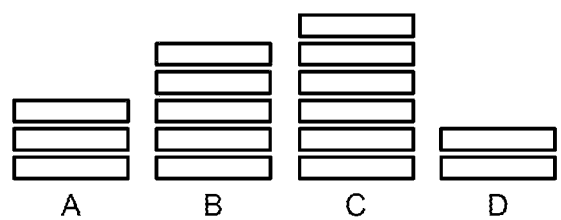
FIG. 9D is a view illustrating a third example of the detection result of the substance to be detected by the plurality of detection cells illustrated in FIG. 9A.

As illustrated in FIG. 9B to FIG. 9D, recognition results are output as a relative intensity display. FIG. 9B illustrates a result where measurement is performed while setting DMMP as the substance to be detected, and FIG. 9C illustrates a result where measurement is performed while setting diphenyl chlorophosphate (dPCP) as the substance to be detected. FIG. 9D illustrates a result where DMMP is detected by a detector in which an equimolar mixture of the organic compound 3 and the organic compound 5 is installed at the detection cell D as the organic probe. As stated above, the intensities different by cells are collectively analyzed to obtain a peculiar signal intensity pattern by the substance to be detected according to the pattern recognition.

The substance to be detected is discriminated based on the signal pattern depending on the signal intensity difference as stated above, and thereby, it is possible to selectively and high sensitively detect the substance to be detected (gas component molecule) having an extremely low concentration in the order of ppt to ppb. Besides, it is possible to further improve the detection sensitivity and the detection accuracy of the substance to be detected (gas component molecule) by increasing the kinds of the organic compounds forming the organic probes. Besides, it is possible to further diversify the peculiar signal patterns by increasing the number of detection cells and installing the organic probes formed of a plurality of organic compounds in one detection cell in addition to increasing the kinds of the organic compounds. Accordingly, it becomes possible to enable the improvement in the detection accuracy of the substance to be detected, and to detect various kinds of substances to be detected 2.

Many of the organophosphorus materials captured by the organic probe are released after the passage of time, but a part thereof is fixed. After a few times of sensing, it becomes necessary to release the organophosphorus materials being the fixed substances to be detected. Gas where 3% of hydrogen at an explosion limit or less is mixed with argon is filled in a firing furnace to be heated, and the substances to be detected which are fixed to the organic probe surface of the sensor are released. This operation is called as reactivation (refresh). It is desired to apply a temperature at approximately 200 to 400° C. for 20 to 30 minutes for the refresh. It is appropriately set in consideration of kinds and disposition states of the organic probes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The inventions described in the accompanying claims and their equivalents are intended to cover such forms or modifications as would fall within the scope and spirit of the inventions.

What is claimed is:

1. A molecular detection apparatus, comprising:
a detector which includes a detection cell having an organic probe,
wherein the organic probe is made of a first organic compound including a head portion which has a monovalent aromatic hydrocarbon group containing a hydroxyl group as a reactive group and a cyano group or a nitro group, a base portion which has a monovalent polycyclic aromatic hydrocarbon group, and a connecting portion which has a bivalent group connecting the head portion and the base portion.

2. The apparatus according to claim 1,
wherein the first organic compound contains a cyanohydrin derivative.

3. The apparatus according to claim 1,
wherein the detection cell includes a sensor unit where the organic probe is provided, and
wherein the sensor unit includes a field effect transistor having a graphene layer and electrodes connected to the graphene layer.

4. The apparatus according to claim 1,
wherein the detector includes a first detection cell which has a first organic probe made of the first organic compound, and a second detection cell which has a second organic probe made of a second organic compound which is different from the first organic compound, and
wherein the second organic compound includes a head portion which has a monovalent aromatic hydrocarbon group containing a hydroxyl group as a reactive group and a trifluoromethyl group, a base portion which has a monovalent polycyclic aromatic hydrocarbon group, and a connecting portion which has a bivalent group connecting the head portion and the base portion.

5. The apparatus according to claim 4,
wherein the detector further includes a third detection cell which does not have the organic probe.

6. The apparatus according to claim 1,
wherein the detector includes a first detection cell which has a first organic probe made of the first organic compound having the cyano group, a second detection cell which has a second organic probe made of the first organic compound having the nitro group, and a third detection cell which has a third organic probe made of a second organic compound which is different from the first organic compound, and
wherein the second organic compound includes a head portion which has a monovalent aromatic hydrocarbon group containing a hydroxyl group as a reactive group and a trifluoromethyl group, a base portion which has a monovalent polycyclic aromatic hydrocarbon group, and a connecting portion which has a bivalent group connecting the head portion and the base portion.

7. The apparatus according to claim 6,
wherein the detector further includes a fourth detection cell which does not have the organic probe.

8. The apparatus according to claim 1,
wherein a substance to be detected is a compound containing phosphorus.

9. The apparatus according to claim 1,
wherein the detector includes a plurality of the detection cells, and
wherein at least one of the detection cells has the organic probe made of the first organic compound.

10. The apparatus according to claim 9, further comprising:

a discriminator which discriminates a substance to be detected by a signal pattern of the plurality of detection cells.

11. The apparatus according to claim 9,
wherein one of the detection cells has a first organic probe made of the first organic compound, and
wherein another one of the detection cells has a second organic probe made of a second organic compound which is different from the first organic compound.

12. The apparatus according to claim 9,
wherein each of the detection cells has the organic probe made of the first organic compound.

13. The apparatus according to claim 1,
wherein the hydroxyl group and the cyano group or the nitro group are bonded to a same carbon in the monovalent aromatic hydrocarbon group.

\* \* \* \* \*